(12) United States Patent
Zhi

(10) Patent No.: US 11,858,938 B2
(45) Date of Patent: Jan. 2, 2024

(54) IMIDAZO-FUSED HETEROCYCLES AND USES THEREOF

(71) Applicant: Ligand Pharmaceuticals Incorporated, San Diego, CA (US)

(72) Inventor: Lin Zhi, San Diego, CA (US)

(73) Assignee: Ligand Pharmaceuticals, Inc., San Diego, CA (US)

(*) Notice: Subject to any disclaimer, the term of this patent is extended or adjusted under 35 U.S.C. 154(b) by 241 days.

(21) Appl. No.: 17/071,273

(22) Filed: Oct. 15, 2020

(65) Prior Publication Data

US 2021/0040102 A1 Feb. 11, 2021

Related U.S. Application Data

(62) Division of application No. 15/070,718, filed on Mar. 15, 2016, now Pat. No. 10,807,983.

(60) Provisional application No. 62/133,935, filed on Mar. 16, 2015.

(51) Int. Cl.
C07D 487/04 (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 10,807,983 | B2 | 10/2020 | Zhi |
| 2005/0153984 | A1 | 7/2005 | Chen |
| 2007/0066577 | A1 | 3/2007 | Choo et al. |
| 2010/0023218 | A1 | 1/2010 | Hayakawa |

FOREIGN PATENT DOCUMENTS

| | | |
|---|---|---|
| EP | 1 674 466 | 6/2006 |
| EP | 2 277 881 | 1/2011 |
| JP | 48-78166 | 10/1973 |
| JP | 2000-086641 | 3/2000 |
| JP | 2008-255024 | 10/2008 |
| RU | 2190611 C2 | 10/2002 |
| WO | WO 87/05297 | 9/1987 |
| WO | WO 97/49704 | 12/1997 |
| WO | WO 99/24035 | 5/1999 |
| WO | WO 03/082272 | 10/2003 |
| WO | WO 05/037285 | 4/2005 |
| WO | WO 05/070906 | 8/2005 |
| WO | WO 07/016392 | 2/2007 |
| WO | WO 07/058482 | 5/2007 |
| WO | WO 07/084542 | 7/2007 |
| WO | WO 07/089512 | 8/2007 |
| WO | WO 04/085425 | 10/2007 |
| WO | WO 08/030579 | 3/2008 |
| WO | WO 08/030584 | 3/2008 |
| WO | WO 09/126635 | 10/2009 |
| WO | WO 09/128520 | 10/2009 |
| WO | WO 10/057121 | 5/2010 |
| WO | WO 2010/100144 | 9/2010 |
| WO | WO 2010/106016 | 9/2010 |
| WO | WO 2010/135014 | 11/2010 |
| WO | WO 2010/144909 | 12/2010 |
| WO | WO 2011/110575 | 9/2011 |
| WO | WO 2012/035055 | 3/2012 |

OTHER PUBLICATIONS

Altland, 1976, Smiles rearrangement of 2-tetrazolylthio-3-aminopyridines, Journal of Organic Chemistry, 41(21):3395-3399.
Arya et al., 1973, Synthesis of new heterocycles. X. Syntheses of thiazolo[5,4-b] pyridines and certain related condensed pyridines, Indian Journal of Chemistry, 11(8):744-746 (abstract).
Balant et al., 1996, Metabolic considerations in prodrug design, in Wolff et al. Burger's Medicinal Chemistry and Drug Discovery, 5th ed. vol. 1: Principles and Practice, pp. 949-982.
Caleta et al., 2009, Novel Cyano- and Amidinobenzothiazole Derivatives: Synthesis, Antitumor Evaluation, and X-ray and Quantitative Structure—Activity Relationship (QSAR) Analysis, J. Med. Chem. 52:1744-1756.
Das et al., Aug. 4, 2003, Discovery of 2-amino-heteroaryl-benzothiazole-6-anilides as potent $p56^{lck}$ inhibitors, Bioorg Med Chem Lett. 13(15):2587-2590.
Dasu et al., 2010, Increased Toll-Like Receptor (TLR) Activation and TLR Ligands in Recently Diagnosed Type 2 Diabetic Subjects, Diabetes Care, 33(4):861-868.
Deng et al, 2003, IL-1 Receptor-associated kinase 1 regulates susceptibility to organ-specific autoimmunity, J Immunol 170:2833-2842.
Dorwald, 2005, Side Reactions in Organic Synthesis, Wiley: VCH Weinheim Preface, pp. 1-15 and 279-308.
Ettmayer et al. May 6, 2004, Lessons Learned from Marketed and Investigational Prodrugs, J. Med. Chem., 47(10):2393-2404.
Greene et al., 1999, Protective Groups in Organic Synthesis, 3rd Edition, John Wiley & Sons, New York, NY, Chapter 1, p. 1-17.
Jordan, Mar. 2003, Tamoxifen: a most unlikely pioneering medicine, Nature Rev. 2:205-213.
Kato et al., 1974, Studies on ketene and its derivatives. LXI. Reaction of primary amine with chloroketene diethylacetal, Kajugaku Zasshi (Journal of the Pharmaceutical Society of Japan), 94(5):627-632.
Khadse et al., 1976, Synthesis and study of 2-arylaminopyrido (3, 2-d)thiazoles as possible anthelmintic agents, Bulletin of Haffkine Institute, 4(1):16-19 (abstract).
Li, 2008, IRAK4 in TLR/IL-1R Signaling: Possible Clinical Applications, European J Immunol, 38:614-618.
Pereira et al., 1987, Dissymmetry of certain substitute dipyrodotetraazapentalenes, Tetrahedron, 43(21):4931-4046.

(Continued)

Primary Examiner — Shobha Kantamneni
(74) Attorney, Agent, or Firm — Knobbe, Martens, Olson & Bear, LLP

(57) ABSTRACT

Compounds and methods in the fields of chemistry and medicine are disclosed. Some of the disclosed embodiments include compounds, compositions and methods of using imidazole-fused heterocycle amines. Some of the disclosed embodiments include imidazo-fused heterocycle compounds useful to treat leukemia and other hematopoietic disorders.

19 Claims, No Drawings

(56) References Cited

OTHER PUBLICATIONS

Qi et al., 2009, Identification of N-(5-tert-Butyl-isoxazol-3-yl)-N'-{4-[7-(2-morpholin-4-yl-ethoxy)imidazo-[2,1-b][1,3]benzothiazol-2-yl]phenyl}urea dihydrochloride (AC220), a uniquely potent, selective and efficacious FMS-like tyrosine kinase-3 (FLT) inhibitors, J. Med. Chem. 52:7808-7816, and supporting information.

Remington's The Science and Practice of Pharmacy, 21st Ed., Lippincott Williams & Wilkins (2006), Table of Content.

Ringwood et al, 2008, The involvement of the interleukin-1 receptor-associated kinases (IRAKs) in cellular signaling networks controlling inflammation, Cytokine 42:1-7.

Sambrook et al. Molecular Cloning: A Laboratory Manual, 2d ed., Cold Spring Harbor Laboratory Press, Cold Spring Harbor, N.Y. (1989).

Sanmiguel et al., 2009, Interleukin-1 regulates keratinocyte expression of T cell targeting chemokines through interleukin-1 receptor associated kinase-1 (IRAK1) dependent and independent pathways, Cellular Signaling, 21:685-694.

Smith et al., 2012, Validation of ITD mutations in FLT3 as a therapeutic target in human acute myeloid leukemia, Nature, 485(7397):260-263.

Song et al., 2009, The kinase activities of interleukin-1 receptor associated kinase (IRAK)-1 and 4 are redundant in the control of inflammatory cytokine expression in human cells, Mol Immunol, 46:1458-1466.

Staschke et al., 2009, IRAK4 kinase activity is required for Th17Differentiation and Th17-mediated disease, J Immunol, 183:568-577.

Stella, 2004, Prodrugs as therapeutics, Expert Opin. Ther. Patents, 14(3):277-280.

Testa, 2004, Prodrug research: futile or fertile? Biochemical Pharmacology, 68:2097-2106.

Vaughan et al., 2010, Molecular mechanism underlying the inflammatory complication of leptin in macrophages, Mol Immunol, 47:2515-2518.

Wang et al., 2006, Crystal Structures of IRAK-4 Kinase in Complex with Inhibitors: A Serine/Threonine Kinase with Tyrosine as a Gatekeeper, Structure, 14:1835-1844.

Wang et al., 2009, IRAK-4 Inhibitors for Inflammation, Curr Topics in Med Chem, 9:724-737.

Yin et al., 2002, Pd-Catalyzed N-Arylation of Heteroarylamines, Org. Lett. 4(20):3481-3484.

Zhang et al., 2009, A Modeling-Derived Hypothesis on Chronicity in Respiratory Diseases: Desensitized Pathogen Recognition Secondary to Hyperactive IRAK/TRAF6 Signaling, PLOS One 4(4):1-7.

Zhang et al., Mar. 24, 2011, Aminothiazolomorphinans with Mixed κ and μ Opioid Activity, J. Med Chem, 54:1903-1913.

Zhu et al., 2010, Toll-Like Receptor Signaling Pathways—Therapeutic Opportunities, Mediators of Inflammation vol. 2010, Article ID 781235, 7 pp.

IMIDAZO-FUSED HETEROCYCLES AND USES THEREOF

INCORPORATION BY REFERENCE TO PRIORITY APPLICATION

The present application is a division of U.S. application Ser. No. 15/070,718, filed Mar. 15, 2016 and to be issued as U.S. Pat. No. 10,807,983, which claims the benefit of priority to U.S. Appl. No. 62/133,935, filed Mar. 16, 2015, each of which is incorporated by reference in its entirety.

FIELD

Compounds and methods in the fields of chemistry and medicine are disclosed. Some of the disclosed embodiments include compounds, compositions and methods of using imidazo-fused heterocycles. Some of the disclosed embodiments include imidazo-fused heterocycles useful to treat hematological malignancy.

BACKGROUND

Fms-like tyrosine kinase 3 (Flt3), also termed as fatal liver kinase-2 (Flt2) is a cytokine receptor whose signaling is part of the normal development of hematopoietic stem cells and progenitor cells. Flt3 is a proto-oncogene and its mutation can lead to certain types of leukemia. Internal tandem duplications of Flt3 (Flt3-ITD) are the most common mutations associated with acute myelogenous leukemia (AML), often associated with a poor prognosis, and has been considered as a therapeutic target (See C. C. Smith, et al. Nature 485: 260-263 (2012)).

Flt3 inhibitors have been developed in different stages of clinical trials for treatment of AML patients with Flt3-ITD mutations. Quizartinib is a small molecule selective class III tyrosine kinase inhibitor including Flt-3 (see C. Qi, et al. J Med Chem 52(23): 7808-16 (2009)). In clinical studies, quizartinib has shown a high rate of response as monotherapy in relapsed/refractory Flt3-ITD positive patients, although quizartinib-resistance mutantions can be developed. There is a need for next generation Flt3 inhibitors that are more selective and less likely to develop resistance.

SUMMARY

Compounds, compositions and methods of using heterocycle amines are disclosed. Some of the disclosed embodiments include imidazo-fused hetereoaryls useful to treat hematopoietic disorders.

Some embodiments described herein are directed to a compound of Formula I:

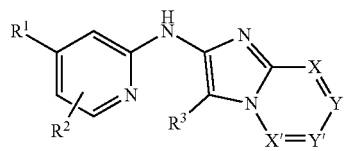

(I)

or a salt, ester, amide, or prodrug thereof,
wherein X is selected from N or $CR^{4a}$; X' is selected from N or $CR^{4b}$; Y is selected from N or $CR^{5a}$; Y' is selected from N or $CR^{5b}$; provided at least one of X, X', Y, and Y' is N;

$R^1$ is selected from the group consisting of hydrogen, halogen, $-OR^6$, $-CN$, $-NR^7R^8$, $-CH_2OR^6$, $-CH_2NR^7R^8$, an optionally substituted $C_{1-6}$ alkyl, an optionally substituted $C_{1-6}$ haloalkyl, an optionally substituted $C_{2-6}$ alkenyl, an optionally substituted $C_{2-6}$ alkynyl, an optionally substituted (5 to 7 membered heterocyclyl)alkyl, an optionally substituted 5 to 7 membered heterocyclyl, an optionally substituted aralkyl; an optionally substituted (5 or 6 membered heteroaryl)alkyl, an optionally substituted $C_{1-6}$ heteroalkyl, $-C(=O)R^6$, $-C(=O)OR^6$, $-C(=O)NR^7R^8$, $-NHC(=O)R^6$, $-SO_2R^6$, and $-SO_2NR^7R^8$;

each of $R^2$, $R^3$, $R^{4a}$ and $R^{4b}$ is independently selected from the group consisting of hydrogen, halogen, $C_{1-6}$ alkyl, OH, and $C_{1-6}$ alkoxy;

each of $R^{5a}$ and $R^{5b}$ is independently selected from the group consisting of hydrogen, halogen, $-OR^6$, $-CN$, $-NR^7R^8$, $-CH_2OR^6$, an optionally substituted aryl, an optionally substituted 5 to 10 membered heteroaryl, an optionally substituted 5-10 membered heterocyclyl, an optionally substituted $C_{3-7}$ carbocyclyl, an optionally substituted $C_{1-6}$ alkyl, an optionally substituted $C_{1-6}$ haloalkyl, an optionally substituted $C_{1-6}$ heteroalkyl, $-C(=O)R^6$, $-C(=O)OR^6$, $-C(=O)NR^7R^8$, $-NHC(=O)R^6$, $-SO_2R^6$, and $-SO_2NR^7R^8$;

each $R^6$ is independently selected from hydrogen, an optionally substituted $C_{1-10}$ alkyl, an optionally substituted $C_{1-10}$ haloalkyl, or an optionally substituted $C_{1-6}$ heteroalkyl; and each $R^7$ and $R^8$ is independently selected from hydrogen; an optionally substituted $C_{1-10}$ alkyl; an optionally substituted $C_{1-10}$ haloalkyl; or an optionally substituted $C_{1-6}$ heteroalkyl; or $R^7$ and $R^8$ are joined together with the nitrogen atom to which they are attached to form an optionally substituted $C_{3-7}$ cycloalkyl or 3 to 7 membered heterocyclyl ring.

In some embodiments, the the compound of Formula (I) is also represented by Formula (II):

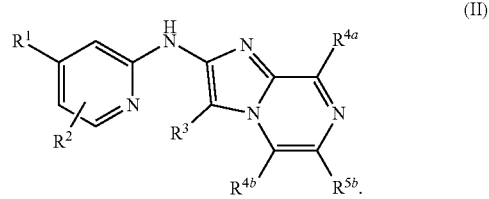

(II)

In some embodiments, the the compound of Formula (I) is also represented by Formula (III):

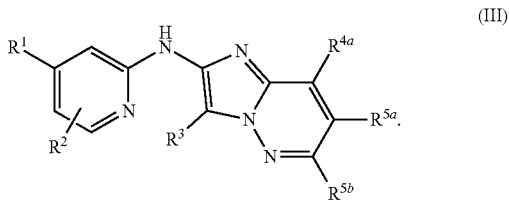

(III)

Some embodiments described herein are directed to pharmaceutical compositions comprising a compound of Formula (I), (II) or (III) as described herein, or a pharmaceutically acceptable salt, ester, amide, or prodrug thereof, and a pharmaceutically acceptable carrier, diluent, excipient or combinations thereof.

Some embodiments described herein are directed to methods of treating a disorder responsive to inhibition of Flt3-mediated signal transduction comprising administering to a subject in need thereof an effective amount of a compound of Formula (I), (II) or (III) as described herein, or a pharmaceutically acceptable salt, ester, amide, or prodrug thereof, or a pharmaceutical composition thereof.

Some embodiments described herein are directed to methods of treating a hematopoietic disorder comprising administering to a subject in need thereof an effective amount of a compound of Formula (I), (II) or (III) as described herein, or a pharmaceutically acceptable salt, ester, amide, or prodrug thereof, or a pharmaceutical composition thereof. In some embodiments, the hematopoietic disorder is selected from the group consisting of certain forms of leukemia, for example, acute myelogenous leukemia (AML).

DETAILED DESCRIPTION

Compounds and methods in the fields of chemistry and medicine are disclosed. Some of the disclosed embodiments include compounds, compositions and methods of using heterocycle amines. Some of the disclosed embodiments include heterocycle amines useful to treat hematopoietic disorders.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference in its entirety for any purpose.

The section headings used herein are for organizational purposes only and are not to be construed as limiting the subject matter described.

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR$^a$ wherein R$^a$ is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like. The term "straight-chain alkoxy" refers to a group comprising the formula: —(CH$_2$)$_p$O— wherein p is any integer. Straight-chain alkoxy does not include substituted or branched alkoxy groups.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "haloalkyl" refers to an alkyl in which at least one hydrogen atom is replaced with a halogen atom. In certain of the embodiments in which two or more hydrogen atoms are replaced with halogen atoms, the halogen atoms are all the same as one another. In certain of such embodiments, the halogen atoms are not all the same as one another.

As used herein, "heteroalkyl" refers to a straight or branched hydrocarbon chain containing one or more heteroatoms, that is, an element other than carbon, including but not limited to, nitrogen, oxygen and sulfur. The heteroalkyl group may have 1 to 20 carbon atom, although the present definition also covers the occurrence of the term "heteroalkyl" where no numerical range is designated. The heteroalkyl group may be designated as "$C_{1-4}$ heteroalkyl" or similar designations. By way of example only, "$C_{1-4}$ heteroalkyl" indicates that there are one to four carbon atoms in the heteroalkyl chain and additionally one or more heteroatoms. In some embodiments, the term "heteroalkyl" refers to an alkyl group comprising two or more carbon atoms in which at least one —CH$_2$— unit of the alkyl group is replaced with a substituent selected from —C=O, —NH—, —S— or —O—; or at least one

unit is replaced with

Examples of heteroalkyls include, but are not limited to, CH$_3$C(=O)CH$_2$—, CH$_3$C(=O)CH$_2$CH$_2$—, CH$_3$CH$_2$C(=O)CH$_2$CH$_2$—, CH$_3$C(=O)CH$_2$CH$_2$CH$_2$—, CH$_3$NHC(=O)CH$_2$—, CH$_3$C(=O)NHCH$_2$—, CH$_3$OCH$_2$CH$_2$—, CH$_3$NHCH$_2$—, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, the term "carbocycle" or "carbocyclyl" refers to non-aromatic cyclic ring or ring system containing only carbon atoms in the ring system backbone. Carbocylic rings may be formed by three, four, five, six, seven, eight, nine, or more than nine carbon atoms. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

As used herein, "cycloalkyl" means a fully saturated carbocyclyl ring or ring system. Examples include cyclopropyl, cyclobutyl, cyclopentyl, and cyclohexyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

An "aralkyl" or "arylalkyl" is an aryl group connected, as a substituent, via an alkylene group, such as "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

The term "heterocycle" or "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocylyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline. Examples of heterocycles include, but are not limited to the following:

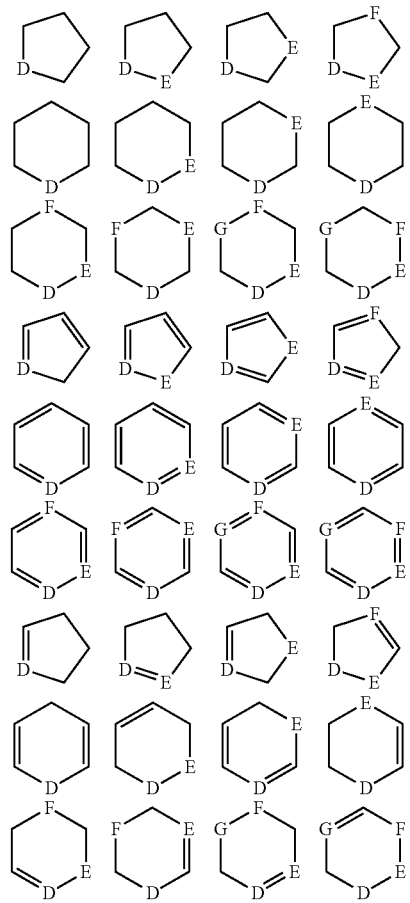

wherein D, E, F, and G independently represent a heteroatom. Each of D, E, F, and G may be the same or different from one another.

A "(heterocyclyl)alkyl" is a heterocyclyl group connected, as a substituent, via an alkylene group. Examples include, but are not limited to, imidazolinylmethyl and indolinylethyl.

The term "heteroatom" refers to an atom other than carbon or hydrogen. Heteroatoms, typically, are independently selected from oxygen, sulfur, nitrogen, and phosphorus, but heteroatoms are not limited to those atoms. In embodiments in which two or more heteroatoms are present, the two or more heteroatoms may all be the same as one another, or some or all of the two or more heteroatoms may each be different from the others.

The substituent "R" appearing by itself and without a number designation refers to a substituent selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

Each of the substituent "$R_A$" and "$R_B$" appearing by itself and without a number designation refers to a substituent independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

The term "O-carboxy" refers to the group consisting of formula RC(=O)O—.

The term "C-carboxy" refers to the group consisting of formula —C(=O)OR.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. Non-limiting examples include formyl, acetyl, propanoyl, benzoyl, and acryl.

The term "acetyl" refers to the group consisting of formula —C(=O)CH$_3$.

The term "trihalomethanesulfonyl" refers to the group consisting of formula X$_3$CS(=O)$_2$— where X is a halogen.

The term "cyano" refers to the group consisting of formula —CN.

The term "cyanato" refers to the group consisting of formula —OCN.

The term "isocyanato" refers to the group consisting of formula —NCO.

The term "thiocyanato" refers to the group consisting of formula —CNS.

The term "isothiocyanato" refers to the group consisting of formula —NCS.

The term "sulfinyl" refers to the group consisting of formula —S(=O)—R.

The term "sulfonyl" refers to the group consisting of formula —S(O)$_2$R.

The term "S-sulfonamido" refers to the group consisting of formula —S(=O)$_2$NR$_A$R$_B$.

The term "N-sulfonamido" refers to the group consisting of formula R$_A$S(=O)$_2$NR$_B$—.

The term "O-carbamyl" refers to the group consisting of formula —OC(=O)—NR$_A$R$_B$.

The term "N-carbamyl" refers to the group consisting of formula R$_B$OC(=O)N(R$_A$)—.

The term "O-thiocarbamyl" refers to the group consisting of formula —OC(=S)—NR$_A$R$_B$.

The term "N-thiocarbamyl" refers to the group consisting of formula R$_B$OC(=S)N(R$_A$)—.

The term "C-amido" refers to the group consisting of formula —C(=O)—NR$_A$R$_B$.

The term "N-amido" refers to the group consisting of formula R$_B$C(=O)N(R$_A$)—.

The term "oxo" refers to the group consisting of formula =O.

The term "carbonyl" refers to the group consisting of formula —C(=O)—.

The term "thiocarbonyl" refers to the group consisting of formula —C(=S)—.

The term "ester" refers to a chemical moiety with formula —COOR, where R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes free amino (i.e., —NH$_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein. A non-limiting example includes carboxyl (i.e., —C(=O)OH).

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —CF$_3$), halo($C_1$-$C_6$)alkoxy (e.g., —OCF$_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

The term "pharmaceutically acceptable carrier" or "pharmaceutically acceptable excipient" as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" as used herein, refer to an amount of a compound sufficient to cure, ameliorate, slow progression of, prevent, or reduce the likelihood of onset of the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

The term "prodrug" refers to a pharmaceutical agent that is converted from a less active form into a corresponding more active form in vivo.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

Compounds

Some embodiments disclosed herein relate to a compound of formula (I) as described above or a pharmaceutically acceptable salt thereof.

In some embodiments, X is N, X' is $CR^{4b}$, Y is $CR^{5a}$, and Y' is $CR^{5b}$. In some such embodiments, $R^{4b}$ is hydrogen. In some such embodiments, $R^{5a}$ is hydrogen. In some such embodiments, $R^{5b}$ is hydrogen.

In some embodiments, X' is N, X is $CR^{4a}$, Y is $CR^{5a}$, and Y' is $CR^{5b}$. In some such embodiments, $R^{4a}$ is hydrogen. In some such embodiments, $R^{5a}$ is hydrogen. In some such embodiments, $R^{5b}$ is hydrogen.

In some embodiments, Y is N, X is $CR^{4a}$, X' is $CR^{4b}$, and Y' is $CR^{5b}$. In some such embodiments, $R^{4a}$ is hydrogen. In some such embodiments, $R^{4b}$ is hydrogen. In some such embodiments, $R^{5b}$ is hydrogen.

In some embodiments, Y is N, X is $CR^{4a}$, X' is $CR^{4b}$, and Y is $CR^{5a}$. In some such embodiments, $R^{4a}$ is hydrogen. In some such embodiments, $R^{4b}$ is hydrogen. In some such embodiments, $R^{5a}$ is hydrogen.

In some embodiments, the compound of Formula (I) is also represented by Formula (II):

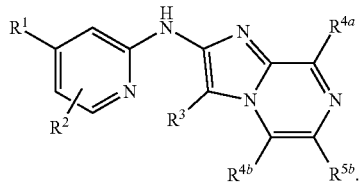
(II)

In some such embodiments, each $R^{4a}$ and $R^{4b}$ is hydrogen.

In some embodiments, the compound of Formula (I) is also represented by Formula (III):

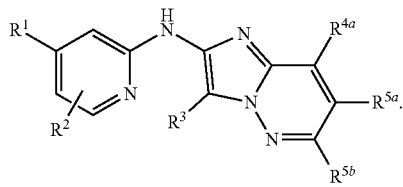
(III)

In some such embodiments, each $R^{4a}$ and $R^{5a}$ is hydrogen.

In some embodiments, $R^1$ is an optionally substituted (5 to 7 membered heterocyclyl)alkyl. In some such embodiments, $R^1$ is an optionally substituted (5 membered heterocyclyl)alkyl. In some such embodiments, $R^1$ is pyrrolidyl-$CH_2$—. In one embodiment, $R^1$ is 1-pyrrolidinyl-$CH_2$—. In some embodiments, $R^1$ is an optionally substituted (6 membered heterocyclyl)alkyl. In some such embodiments, $R^1$ is selected from piperidinyl-$CH_2$— or morpholine-$CH_2$—. In one embodiment, $R^1$ is 1-piperidinyl-$CH_2$—. In another embodiment, $R^1$ is 1-morpholino-$CH_2$—. In some embodiments, $R^1$ is an optionally substituted 5 to 7 membered heterocyclyl. In some sucy embodiments, $R^1$ is an optionally substituted 6 membered heterocyclyl. In some such embodiments, $R^1$ is selected from optionally substituted morpholinyl, optionally substituted piperazinyl, or optionally substituted piperidinyl. In one embodiment, $R^1$ is 1-morpholinyl. In another embodiment, $R^1$ is 4-substituted-piperazin-1-yl. In yet another embodiment, $R^1$ is and 1-substituted-piperidin-4-yl.

In some embodiments, $R^2$ is hydrogen. In some embodiments, $R^3$ is hydrogen. In some further embodiments, both $R^2$ and $R^3$ are hydrogen.

In some embodiments, $R^{5a}$ is hydrogen and $R^{5b}$ is selected from CN or an optionally substituted 5 to 10 membered heteroaryl. In some such embodiments, $R^{5b}$ is an optionally substituted 6 membered heteroaryl. In some such embodiments, $R^{5b}$ is selected from pyridyl, pyrimidyl, pyrazinyl, or pyridazinyl. In some other embodiments, $R^{5b}$ is an optionally substituted 5 membered heteroaryl. In one such embodiment, $R^{5b}$ is pyrazolyl.

In some embodiments, the compound of formula (I) is selected from

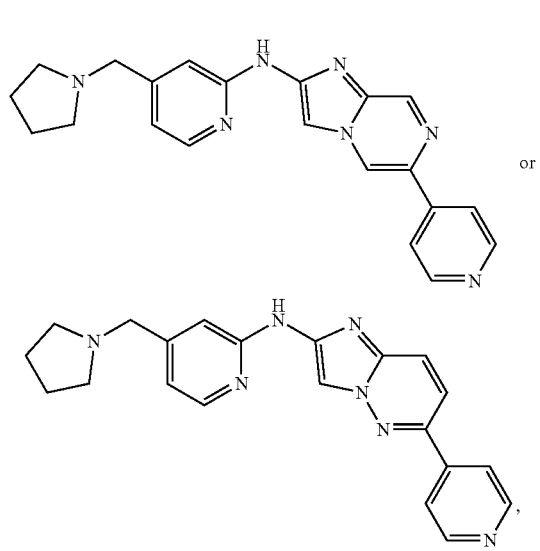
or or pharmaceutically acceptable salts, esters, amides, or prodrugs thereof.

Exemplary Synthetic Methods

In certain embodiments, compounds of the present invention can by synthesized using the following Schemes.

Scheme I

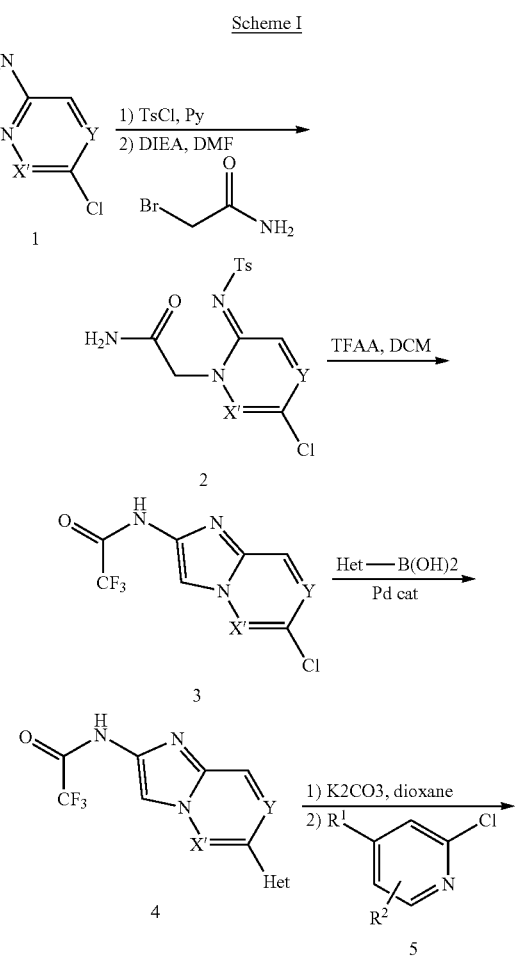

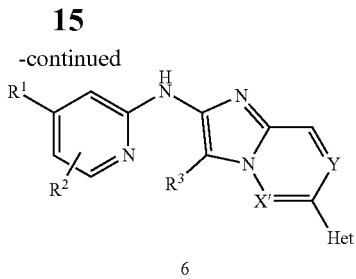

6

Scheme I describes general synthesis of the 2-(2-pyridinylamino)imidazo[1,2-a]pyrazines or 2-(2-pyridinylamino)imidazo[1,2-a]pyridazines of structure 6. An aminopyridazine of structure 1 is treated sequentially with TsCl and 2-bromoacetamide in the presence of bases to afford an intermediate o structure 2. Treatment of the intermediate of structure 2 with trifluoroacetic acid generates a bicyclic compound of structure 3. Palladium catalyzed coupling of structure 3 with a boronic acid affords a compound of structure 4. Deprotection of the trifluoroacetyl group followed by treatment of a 2-chloropyridine compound of structure 5 yield the final product of structure 6.

One of skill in the art will recognize that analogous synthetic schemes may be used to synthesize similar compounds. One of skill will recognize that compounds of the present invention may be synthesized using other synthesis schemes. In certain embodiments, the invention provides a salt corresponding to any of the compounds provided herein.

Certain Pharmaceutical Compositions

Some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In certain embodiments, a pharmaceutical composition comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical composition comprising one or more compounds of the present embodiments is a liquid (e.g., a suspension, elixir and/or solution). In certain of such embodiments, a liquid pharmaceutical composition comprising one or more compounds of the present embodiments is prepared using ingredients known in the art, including, but not limited to, water, glycols, oils, alcohols, flavoring agents, preservatives, and coloring agents.

In certain embodiments, a pharmaceutical composition comprising one or more compounds of the present embodiments is a solid (e.g., a powder, tablet, and/or capsule). In certain of such embodiments, a solid pharmaceutical composition comprising one or more compounds of the present embodiments is prepared using ingredients known in the art, including, but not limited to, starches, sugars, diluents, granulating agents, lubricants, binders, and disintegrating agents.

In certain embodiments, a pharmaceutical composition comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition comprising one or more compounds of the present embodiments comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition comprising one or more compounds of the present embodiments comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in the pharmaceutical composition of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical composition comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical composition comprising one or more compounds of the present embodiments is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical composition comprising one or more compounds of the present embodiments is useful for treating a condition or disorder in a mammal, such as a human. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition comprising a compound of the present embodiments is prepared for oral administration. In certain of such embodiments, a pharmaceutical composition is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical compositions for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, New Jersey), hydrophilic ointment (USP) and Lubriderm™, available from Pfizer (Morris Plains, New Jersey).

In certain embodiments, the formulation, route of administration and dosage for a pharmaceutical composition of the present embodiments can be chosen in view of a particular patient's condition. In certain embodiments, a pharmaceutical composition is administered as a single dose. In certain embodiments, a pharmaceutical composition is administered as a series of two or more doses administered over one or more days.

In certain embodiments, a pharmaceutical composition of the present embodiments is administered for a period of continuous therapy. For example, a pharmaceutical composition of the present embodiments may be administered over a period of days, weeks, months, or years.

In certain embodiments, a pharmaceutical composition may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical composition is in powder form for constitution with a suitable vehicle, e.g., sterile pyrogen-free water, before use.

The compounds are administered at a therapeutically effective dosage, e.g., a dosage sufficient to provide treatment for the disease states previously described. While human dosage levels have yet to be optimized for the compounds of the preferred embodiments, generally, a daily dose for most of the compounds described herein is from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarilly, vaginally, rectally, or intraocularly. Oral and parenteral administrations are customary in treating the indications that are the subject of the preferred embodiments.

Certain Therapeutic Methods

Some compounds and compositions provided herein, such as compounds and/or compositions comprising Formula I are useful for the treatment of a variety of diseases and disorders malignant or benign hematopoietic disorders. Examples of leukemia include acute lymphocytic leukemia (ALL), chronic lymphocytic leukemia (CLL), acute myelogenous leukemia, chronic myelogenous leukemia (CML), chronic idiopathic myelofibrosis, chronic neutrophilic leukemia (CNL), and acute monocytic leukemia.

In some embodiments, the compounds and compositions provided herein can be administered in combination with one or more additional anticancer agent(s) or treatment. Examples of other anticancer agents or treatment include HDAC inhibitors, chemotherapy, immunotherapy, VEGFR modulators, bone marrow transplant, and stem cell transplant.

EXAMPLES

The following examples, including experiments and results achieved, are provided for illustrative purposes only and are not to be construed as limiting the present invention. Where chemical structures depict atoms having an unfilled valency, it is to be understood that the valency is satisfied with one or more hydrogen atoms.

Example 1

6-(4-Pyridinyl)-2-(4-(1-pyrrolidinylmethyl)-2-pyridinyl)imidazo[1,2-a]pyrazine (Compound 101)

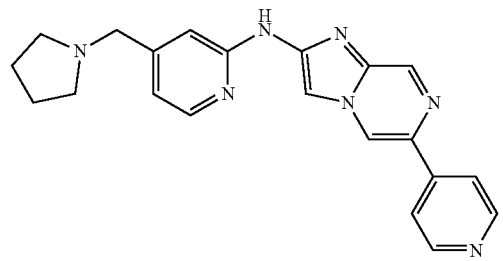 [SMILES: c1cc(-c2cn3cc(Nc4cc(CN5CCCC5)ccn4)nc3cn2)ccn1]

Compound 101 was prepared according to the general procedure described in Scheme I from 5-bromopyrazin-2-amine as follows.

Preparation of 2-(5-bromo-2-(tosylimino)pyrazin-1 (2H)-yl)acetamide (Compound 2A)

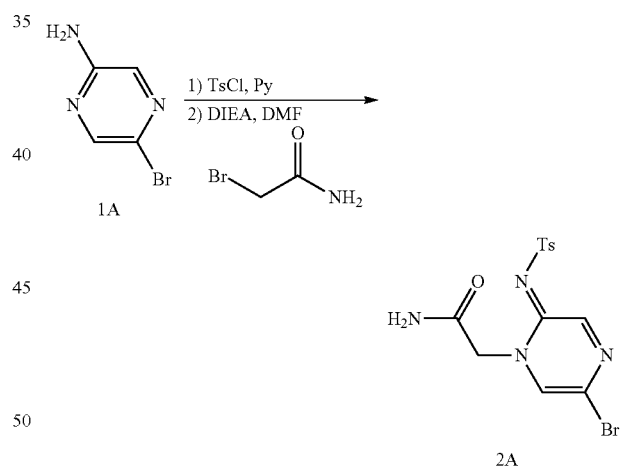

A mixture of 5-bromopyrazin-2-amine (2.8 g, 16 mmol) and TsCl (3.7 g, 19 mmol) in pyridine (50 mL) was stirred at 90° C. for 5 h. The residue was concentrated under reduce pressure. The residue was diluted with 100 mL of water and the solid formed was collected, washed with water, and dried under vacuum to give the N-tosyl 5-bromopyrazin-2-amine (4.5 g, 85%). A mixture of the N-tosyl intermediate (4.5 g, 14 mmol), bromoacetamide (2.1 g, 15 mmol), and DIEA (1.9 g, 15 mmol) in DMF (60 mL) was stirred at room temperature for 48 h. The residue was poured into 300 mL water and the resulting solid was filtered and dried under vacuum to give Compound 2A (4.7 g, 87% yield).

Preparation of 6-(pyridin-4-yl)imidazo[1,2-a]pyrazin-2-amine (Compound 4A)

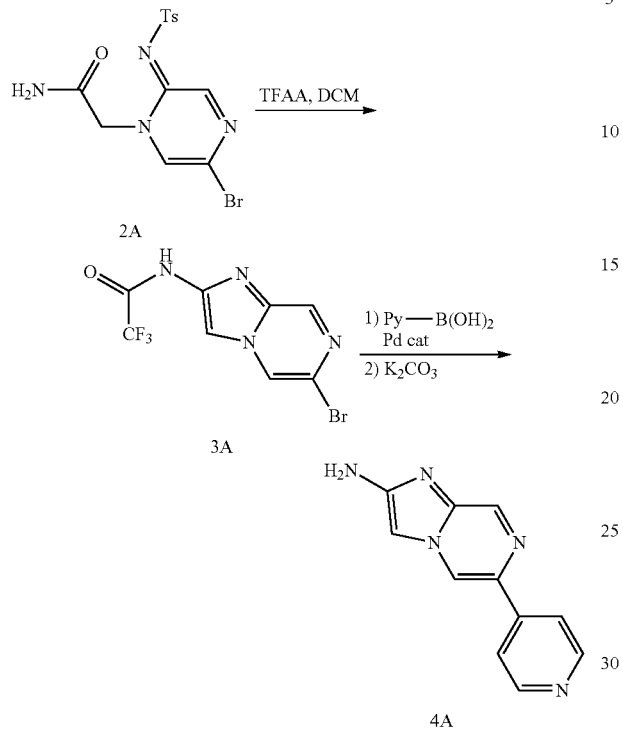

To a suspension of Compound 2A (4.7 g, 12 mmol) in DCM (60 mL) was added TFAA (10 mL) and the resulting mixture was stirred at room temperature for 3 hours. The mixture was concentrated and diluted with 100 mL of aqueous NaHCO$_3$. The crude mixture was purified by column chromatography (PE/EA=5/1) to give Compound 3A as white solid (1.3 g, 35% yield). A mixture of Compound 3A (463 mg, 1.5 mmol), boronic acid (246 mg, 2 mmol), PdCl$_2$(PPh$_3$)$_2$ (210 mg, 0.3 mmol), and K$_2$CO$_3$ (1.2 g, 4.5 mmol) in dioxane/water (5/1, 12 mL) was stirred at 100° C. in a microwave reactor for 2 hours. The mixture was concentrated and treated with K$_2$CO$_3$ (1.4 g, 10 mmol) in dioxane/water (1/1, 20 mL) at 100° C. for 2 hours. After concentrated, the residue was stirred with 20 mL MeOH to form a crude solid that was purified by prep-HPLC (basic condition) to give Compound 4A (260 mg, 82%).

Preparation of 6-(4-pyridinyl)-2-(4-(1-pyrrolidinylmethyl)-2-pyridinyl)imidazo[1,2-a]pyrazine (Compound 101)

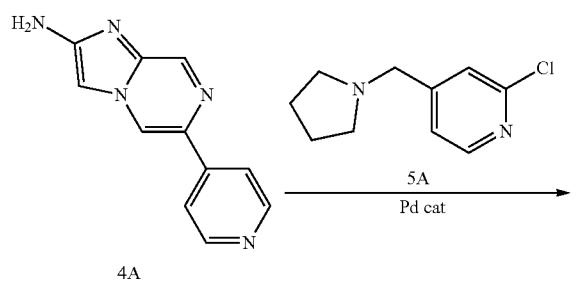

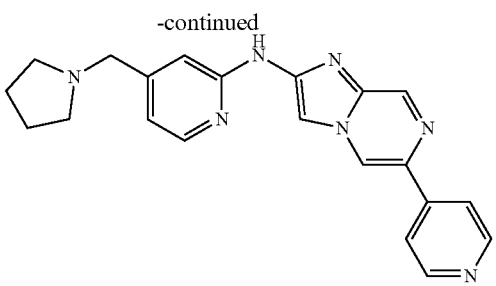

A mixture of Compound 4A (100 mg, 0.47 mmol) and Compound 5A (100 mg, 0.51 mmol), BINAP (20 mg, 0.032 mmol), Pd$_2$(dba)$_3$ (20 mg, 0.022 mmol), Cs$_2$CO$_3$ (307 mg, 0.95 mmol) in dioxane (10 mL) was stirred at 100° C. for 12 hours. The reaction mixture was concentrated and purified by prep-HPLC to give the desired compound as yellow solid (35 mg, 18% yield). $^1$H-NMR (400 MHz, MeOD) 9.66 (d, J=1.2, 1H), 9.26 (s, 1H), 8.93 (d, J=6.4, 1H), 8.78 (d, J=6.8, 1H), 8.44 (d, J=6.4, 1H), 7.67 (s, 1H), 7.44 (dd, J=6.4 and 1.2, 1H), 4.62 (s, 2H), 3.80-3.55 (m, 4H), and 2.30-2.10 (m, 4H).

Example 2

6-(4-Pyridinyl)-2-(4-(1-pyrrolidinylmethyl)-2-pyridinyl)imidazo[1,2-a]pyridazine (Compound 102)

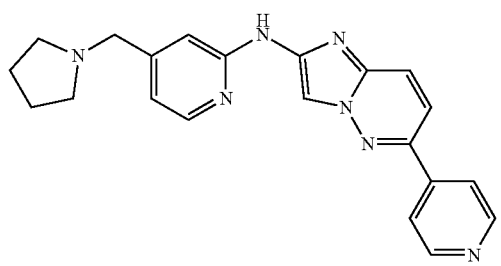 [SMILES: c1cc(-c2ccc3nc(Nc4cc(CN5CCCC5)ccn4)cn3n2)ccn1]

Preparation of 2-(5-bromo-2-(tosylimino)pyrazin-1(2H)-yl)acetamide (Compound 2B)

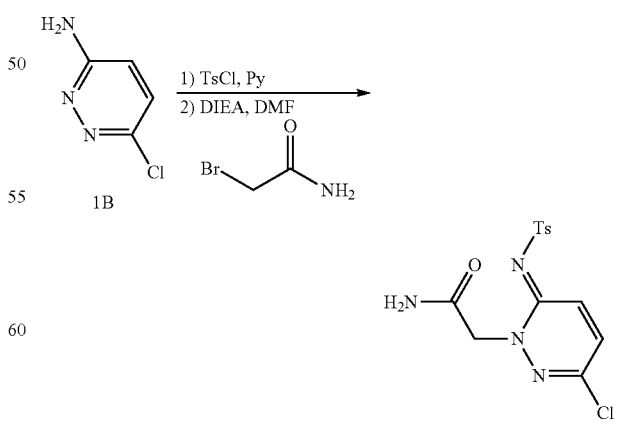

A mixture of Compound 1B (6.8 g, 52 mmol) and TsCl (11 g, 57 mmol) in pyridine (60 mL) was stirred at 90° C.

for 4 h. The mixture was concentrated under reduce pressure and diluted with 50 mL water to form the crude solid. The solid was washed with water and dried under vacuum to give the N-tosyl intermediate (10 g, 67%). A mixture of the N-tosyl intermediate (4.0 g, 14 mmol), bromoacetamide (2.2 g, 16 mmol), and DIEA (2.0 g, 16 mmol) in DMF (30 mL) was stirred at room temperature for 8 hours. The mixture was poured into 200 mL of ice water and stirred for 0.5 hour. The resulting solid was filtered and dried under vacuum to give Compound 2B (4.3 g, 89% yield).

Preparation of 6-(pyridin-4-yl)imidazo[1,2-a]pyrazin-2-amine (Compound 4B)

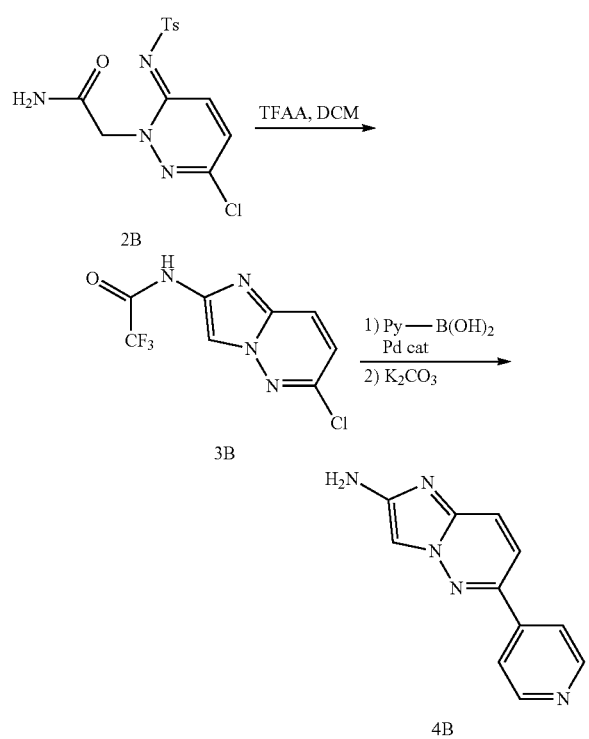

To a suspension of Compound 2B (2.0 g, 5.9 mmol) in DCM (30 mL) was added TFAA (10 mL). The mixture was stirred at room temperature for 3 hours. The reaction mixture was concentrated and diluted with 50 mL of aqueous NaHCO$_3$ to gave the crude solid, and further purification by column chromatography (PE/EA=5/1) afforded Compound 3B as white solid (1.3 g, 85% yield). A mixture of Compound 3B (529 mg, 2.0 mmol), 4-pyridineboronic acid (369 mg, 3.0 mmol), PdCl$_2$(PPh$_3$)$_2$ (280 mg, 0.4 mmol), and K$_2$CO$_3$ (552 mg, 4.0 mmol) in dioxane/water (4/1, 15 mL) was stirred at 100° C. in a microwave reactor for 1.5 hours. The reaction mixture was concentrated and purified by column (PE/EA=1/1 then DCM/MeOH=20/1) to give N-trifluoroacetyl protected Compound 4B as a yellow solid (250 mg, 40% yield). Deprotection reaction with K$_2$CO$_3$ (817 mg, 5.9 mmol) in dioxane/MeOH/H$_2$O (1/1/1, 30 mL) at 100° C. for 1 hour to give Compound 4B as a solid (80 mg, 46% yield).

Preparation of 6-(4-Pyridinyl)-2-(4-(1-pyrrolidinylmethyl)-2-pyridinyl)imidazo[1,2-a]pyridazine (Compound 102)

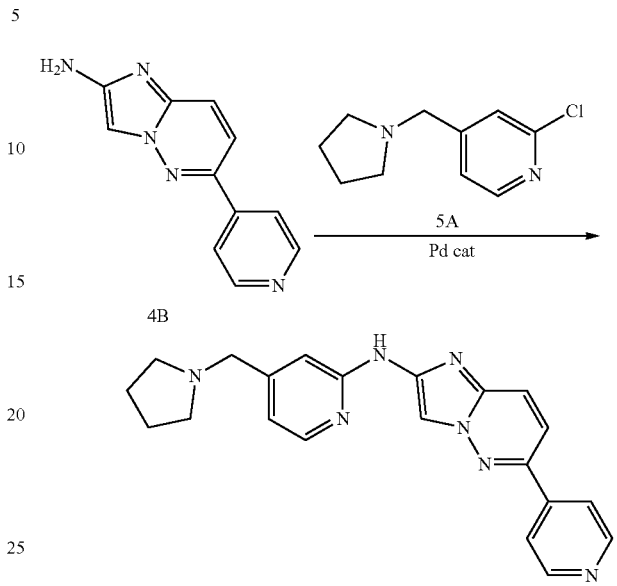

A mixture of Compound 4B (80 mg, 0.38 mmol), Compound 5A (80 mg, 0.41 mmol), BINAP (15 mg, 0.024 mmol), Pd$_2$(dba)$_3$ (15 mg, 0.016 mmol), Cs$_2$CO$_3$ (246 mg, 0.76 mmol) in dioxane (5 mL) was stirred at 100° C. for 12 h. The reaction mixture was concentrated and purified by prep-HPLC to give Compound 102 as yellow solid (30 mg, 21% yield). $^1$H-NMR (400 MHz, DMSO-d6) 11.85 (bs, 1H), 11.11 (s, 1H), 9.26 (s, 1H), 9.04 (d, J=4.4, 2H), 8.63 (t, J=6.4, 2H), 8.38 (d, J=5.6, 1H), 8.21 (d, J=9.6, 1H), 8.12 (d, J=9.2, 1H), 7.41 (d, J=5.6, 1H), 7.33 (s, 1H), 4.40 (d, J=5.6, 2H), 3.40 (bs, 2H), 3.06 (bs, 2H), and 2.02-1.91 (m, 4H).

Example 3

The following inhibitory assay is useful for evaluating test compounds for inhibition of Flt3 kinase activity. The assay is performed using traditional radioisotope filtration binding.

A base reaction buffer is prepared consisting of 20 mM Hepes (pH 7.5), 10 mM MgCl$_2$, 1 mM EGTA, 0.02% Brij35, 0.02 mg/ml BSA, 0.1 mM Na$_3$PO$_4$, 2 mM DTT, 1% DMSO. The peptide substrate abltide [EAIYAAPFAKKK] is added to the base reaction buffer to yield a final concentration of 5 μM. Additional cofactors (1.5 mM CaCl$_2$, 16 ug/ml Calmodulin, and 2 mM MnCl$_2$) are added to the buffer/substrate solution. Recombinant human FLT3 (baculovirus expression system using a C-terminal His6-tag) is added to the solution and gently mixed. Test compounds are dissolved in DMSO and added to the buffer/kinase solution to yield a final concentration of 5 μM. Compounds were tested in a 10-dose IC50 in duplicate with 3-fold serial dilution starting at 1 μM to yield a full dose response curve. Staurosporine was used as positive control with a 10-dose IC50 with 3-fold serial dilution starting at 20 μM to yield a dose response curve. The reaction is initiated by the addition of $^{33}$P-ATP (specific activity 500 Ci/μl) into the reaction mixture to a final concentration of 10 μM. The kinase reaction was incubated for 120 minutes at room temperature. The reactions are spotted onto P81 ion exchange paper (Whatman #3698-915) and the filter papers are extensively washed in 0.75%

Phosphoric acid and beta emissions are measured. Flt3 inhibition IC50 values of the compounds are in the table below.

| Number | Flt3 inhibition IC$_{50}$ (nM) |
|---|---|
| Compound 101 | 0.11 |
| Compound 102 | 0.25 |
| Staurosporine | <1.0 |

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A compound of Formula (III):

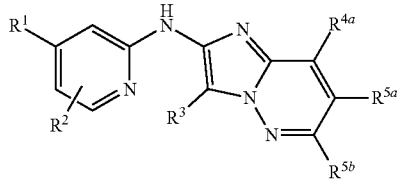

(III)

or a pharmaceutically acceptable salt, ester, amide, or prodrug thereof,
wherein
R$^1$ is selected from the group consisting of an optionally substituted (5 to 7 membered heterocyclyl)alkyl, an optionally substituted aralkyl; and an optionally substituted (5 or 6 membered heteroaryl)alkyl;
each of R$^2$, R$^3$, and R$^{4a}$ is independently selected from the group consisting of hydrogen, halogen, C$_{1-6}$ alkyl, OH, and C$_{1-6}$ alkoxy;
each of R$^{5a}$ and R$^{5b}$ is independently selected from the group consisting of hydrogen, halogen, —OR$^6$, —CN, —NR$^7$R$^8$, —CH$_2$OR$^6$, an optionally substituted aryl, an optionally substituted 5 to 10 membered heteroaryl, an optionally substituted 5-10 membered heterocyclyl, an optionally substituted C$_{3-7}$ carbocyclyl, an optionally substituted C$_{1-6}$ alkyl, an optionally substituted C$_{1-6}$ haloalkyl, an optionally substituted C$_{1-6}$ heteroalkyl, —C(=O)R$^6$, —C(=O)OR$^6$, —C(=O)NR$^7$R$^8$, —NHC(=O)R$^6$, —SO$_2$R$^6$, and —SO$_2$NR$^7$R$^8$;
each R$^6$ is independently hydrogen, an optionally substituted C$_{1-10}$ alkyl, an optionally substituted C$_{1-10}$ haloalkyl, or an optionally substituted C$_{1-6}$ heteroalkyl; and
each R$^7$ and R$^8$ is independently selected from hydrogen; an optionally substituted C$_{1-10}$ alkyl; an optionally substituted C$_{1-10}$ haloalkyl; or an optionally substituted C$_{1-6}$ heteroalkyl; or R$^7$ and R$^8$ are joined together with the nitrogen atom to which they are attached to form an optionally substituted C$_{3-7}$ cycloalkyl or 3 to 7 membered heterocyclyl ring.

2. The compound of claim 1, wherein each of R$^{4a}$ and R$^{5a}$ is hydrogen.

3. The compound of claim 1, wherein R$^1$ is an optionally substituted (5 to 7 membered heterocyclyl)alkyl.

4. The compound of claim 3, wherein R$^1$ is an optionally substituted (5 membered heterocyclyl)alkyl.

5. The compound of claim 4, wherein R$^1$ is pyrrolidyl-CH$_2$—.

6. The compound of claim 3, wherein R$^1$ is an optionally substituted (6 membered heterocyclyl)alkyl.

7. The compound of claim 6, wherein R$^1$ is piperidinyl-CH$_2$— or morpholine-CH$_2$—.

8. The compound of claim 1, wherein R$^2$ is hydrogen.

9. The compound of claim 1, wherein R$^3$ is hydrogen.

10. The compound of claim 1, wherein R$^{5b}$ is an optionally substituted 5 to 10 membered heteroaryl.

11. The compound of claim 10, wherein R$^{5b}$ is an optionally substituted 6 membered heteroaryl.

12. The compound of claim 11, wherein R$^{5b}$ is pyridyl, pyrazinyl, pyridazinyl, or pyrimidyl.

13. The compound of claim 10, wherein R$^{5b}$ is an optionally substituted 5 membered heteroaryl.

14. The compound of claim 13, wherein R$^{5b}$ is pyrazolyl.

15. The compound of claim 1, having the structure

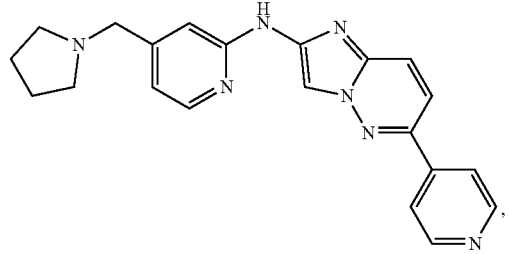 [SMILES: c1cc(-c2ccc3nc(Nc4cc(CN5CCCC5)ccn4)cn3n2)ccn1]

or a pharmaceutically acceptable salt, ester, amide, or prodrug thereof.

16. A pharmaceutical composition comprising an effective amount of a compound of claim 1, or a pharmaceutically acceptable salt, ester, amide, or prodrug thereof, and one or more pharmaceutically acceptable carriers, diluents, excipients, or combinations thereof.

17. The compound of claim 2, wherein R$^1$ is an optionally substituted (5 to 7 membered heterocyclyl)alkyl.

18. The compound of claim 17, wherein R$^1$ is an optionally substituted (5 membered heterocyclyl)alkyl.

19. The compound of claim 18, wherein R$^1$ is pyrrolidyl-CH$_2$—.

* * * * *